United States Patent [19]
Wintrich et al.

[11] Patent Number: 5,551,780
[45] Date of Patent: Sep. 3, 1996

[54] METHOD TO DETERMINE CHARACTERISTIC FEATURES OF PROCESSES FORMING RADICALS

[75] Inventors: Franz Wintrich, Essen; Dieter Kaiser, Dortmund; Holger Eisenloher, Heiligenhaus; Kurt-Henry Mindermann, Ratingen, all of Germany

[73] Assignee: RWE Entsorgung, Germany

[21] Appl. No.: 198,102

[22] Filed: Feb. 17, 1994

[30] Foreign Application Priority Data

Feb. 24, 1993 [DE] Germany ............... 43 05 645.8

[51] Int. Cl.⁶ .................... G01N 21/00; G01J 5/00
[52] U.S. Cl. .................. 374/45; 374/142; 374/129; 374/121; 250/424
[58] Field of Search .................. 374/142, 121, 374/129, 45, 127, 124; 250/424

[56] References Cited

U.S. PATENT DOCUMENTS

| | | | |
|---|---|---|---|
| 3,492,869 | 2/1970 | Toyota et al. | 374/129 |
| 3,539,807 | 11/1970 | Bickel | 374/129 |
| 3,611,806 | 10/1971 | Hishikari | 374/129 |
| 3,806,249 | 4/1974 | Lesinski | 374/127 |
| 4,066,904 | 1/1978 | Bertaux et al. | 250/372 |
| 4,466,748 | 8/1984 | Needham | 374/129 |
| 4,779,977 | 10/1988 | Rowland et al. | 374/127 |

FOREIGN PATENT DOCUMENTS 0147818  1/1962  U.S.S.R. ............... 374/129

*Primary Examiner*—Diego F. F. Gutierrez
*Attorney, Agent, or Firm*—Connolly & Hutz

[57] ABSTRACT

A method for determining characteristic features of processes forming radicals by sensing the temperature and/or the concentration of radicals with detectors in zones that are monitored by at least 2 detectors.

6 Claims, 1 Drawing Sheet

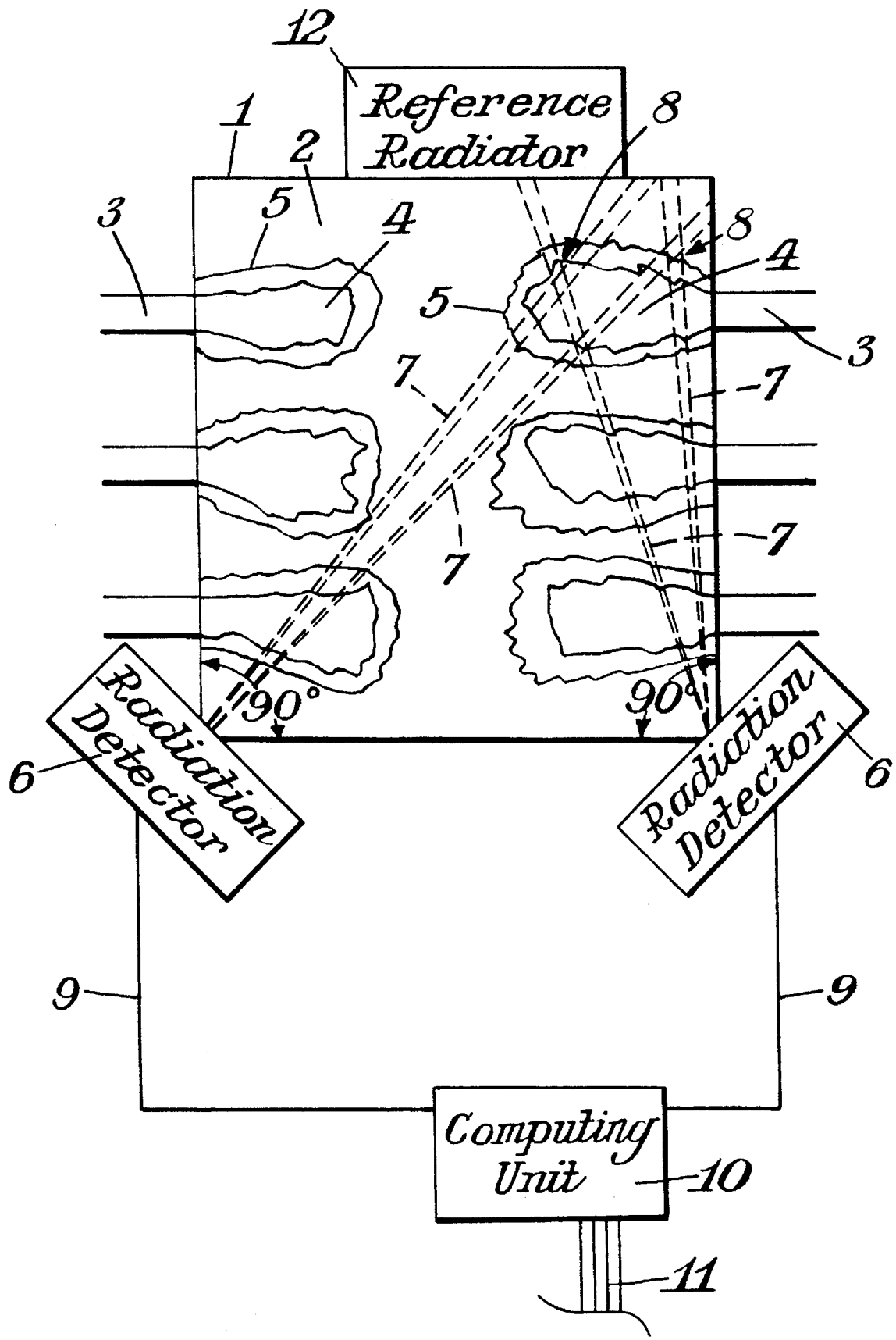

METHOD TO DETERMINE CHARACTERISTIC FEATURES OF PROCESSES FORMING RADICALS

BACKGROUND OF THE INVENTION

The present invention relates to a method to determine characteristic features of processes forming radicals.

Forming of radicals occurs in numerous thermal and/or chemical conversions as for instance in the combustion of fossil fuels, such as hard or brown coal, heavy oil, natural gas, in the combustion of sewage sludge, waste or hazardous waste, in the gasification of materials containing carbon and also in other chemical and/or thermal processes.

In order to control methods comprising such processes, characteristic features of the respective process are recorded and then generally evaluated correspondingly, for instance in order to form command variables for a process control, especially in view of $NO_x$ and 2,3,7,8 TCDD and dibenzofuran production. Thereby, the recorded characteristic features can directly and/or indirectly form command variables, i.e. for instance after calculation of a basic number.

Various methods to determine the temperature as a characteristic feature are known. With a method operating with a suction pyrometer for instance, a cooled lance is held in a reaction space through the sight hole of a reactor, and the temperature of the sucked off gas quantity determined. Hereby, only a single local temperature will be determined in spite of the high measuring expenditure, whereby the determination in addition contains faults since inserting the lance itself influences the measuring result. Moreover, this method enables only a subsequent evaluation of the temperature which can be allocated locally in the reaction space only inaccurately, and the lance is exposed to high thermal stresses and wear.

For determination of the temperature of chemical and/or thermal processes, contactless methods are also known. It has been proposed to arrange a multitude of acoustic source detector units in a plane outside of the wall surrounding the combustion chamber for contactless determination of the temperature in the combustion chamber of a coal-fired power plant. In this method a source detector unit transmits a short-time acoustic signal such as a bang which is received by the other source detector units. Transmitting and receiving acoustic signals are then exchanged cyclically until each unit has transmitted once and the other units have received correspondingly often. The momentary density of combustion gases and then the temperature of which are concluded from the varying speeds of the sound conveyance through the combustion chamber. This method has the disadvantage that only mean temperature values can be determined since sound waves excited by the source detector units pass only partially through the whole combustion chamber in which, however, the temperature is distributed heterogeneously and not homogeneously, resulting in zones having varying densities of combustion gases. Additionally, dust and skin formations interfere with exact temperature determination.

The determination of radicals generated in combustion processes to control waste combustion processes is also known according to EP-A-0 317 731.

In view of measuring methods inside the combustion chamber of e.g. waste combustion plants, which have been unsatisfactory up to now, exact analyses of the function leading to contaminant formation are still not available.

Especially the detection of local conditions in the conversions previously mentioned is not satisfactorily possible.

SUMMARY OF THE INVENTION

Therefore, the object of the present invention is to provide an improved method to determine characteristic features of processes operating at high temperatures.

This object will be achieved by a method to determine characteristic features of processes generating radicals, characterized in that temperature and/or concentration of radicals are sensed by detectors in zones that can be monitored by at least two detectors.

Since the radiation spectrum in zones comprising radicals is sensed by at least two detectors, spatially inhomogeneous state variables and kinetic formation processes can be taken into consideration. The evaluation of the radiation spectrum in such zones ensures the exact determination of local state variables and local formation processes. The determination of temperatures in the zones and/or of the concentration of radicals in the zones provides essential features of processes generating radicals and basic factors for its evaluation and control. Hereby, the checking of $NO_x$ production is of special importance. The knowledge of temperature and radical concentration conditions in the zones permits to reveal local process sequences in a way that enables to intervene purposefully in local process sequences. Hereby, the intervention may take place for instance by triggering of combustion air nozzles, fuel supply, recirculation of waste gases, fuel distribution, temperature of the supplied combustion air, or eventually by injection of $NH_3$.

The present invention enables to determine intentionally sections from the process space by limiting the radiation incidenting in the detectors, the evaluation of which is of special importance. This may take place for instance by limiting the angle of incidence, e.g. through a slot.

A radiation spectrum can be generated in thermally and chemically excited radiation respectively in reaction zones of a combustion chamber, whereby for instance one burner near field can be detected. Any kind of gas emits band radiation with discrete wavelengths based on quantized energy contributions from rotation, vibration and electronic excitation. Chemical energy released in combustion enables the electronic excitation of molecules. Such an excitation is followed by a spontaneous emission, generally in the UV range.

Band emission of individual molecules as well as structure-borne radiation essentially free of bands, e.g. particle radiation from dust, can be detected by determination of the radiation spectrum according to the invention, thus enabling to define exactly the concentration of radicals with the application of the mentioned method. In addition, a spectroscopic examination of the self-glow of a flame and the pyrometric determination of a flame temperature can be performed simultaneously in burner-aided processes. With the detection of radicals, the evaluation of the radiation spectrum in the zones permits to establish and quantify disturbing influences by for instance soot and/or dust radiation in such a way, that the accuracy of temperature determination and the determination of radical concentrations will be essentially improved.

Another advantage of the method consists of the isochronous detection of radiation spectra in multiple zones which ensures the determination of isochronous, locally characteristic features. The isochronous detection enables also to record momentarily temperature conditions and formation processes in any areas at one point of time.

The radiation spectrum may comprise a wavelength range in which band radiation of radicals typically for a process occurs. In combustion processes it is suitable to detect a range of approximately 200 to 520 nm. A range of approximately 300 to 480 nm for instance is suitable for the determination in the near field of a dust burner in coal combustion, whereby among other things intensity peaks of CO, $C_2$, CN, CH are present in this range.

The detection of a reference radiation, which is emitted from a reference radiator radiating in a defined wavelength range, may also be provided in addition for a temporary or permanent balancing and calibration respectively of the detection and/or for improving the evaluation of the radiation spectrum. The wavelength range may thereby advantageously be outside of or also between characteristic band radiation of radicals, which makes evaluation and identification respectively easier.

The detection of reference radiation provides additional information for taking into account disturbing influences when detecting radicals, thus enabling to estimate for instance dust and/or soot loads more accurately. In this connection it may be also useful to determine and evaluate the absorption of the reference radiation.

An embodiment example of a facility with application of the method according to the invention is represented in the attached drawing and will be described in the following.

BRIEF DESCRIPTION OF THE DRAWING

The FIGURE shows schematically a section through a combustion chamber of a coal-fired combustion plant.

DETAILED DESCRIPTION OF THE INVENTION

In a combustion chamber 2 surrounded by a wall 1, fuel and combustion air are supplied through burner facilities 3 comprising air supply conduits and burned under generation of flames 4. Radical zones 5, which contain the flames 4, comprise the radicals generated in combustion.

Two detectors 6 interspaced of each other are arranged on two adjacent edges of the in section substantially rectangularly shaped wall 1. Each detector 6 senses in the radical zones 5 radiation spectra and intensities respectively along radiation directions, which run essentially in fan shape, and form respective axes of conical sections 7 of the combustion chamber 2. The sections 7 intersecting in the combustion chamber 2 detect the detecting zones 8 according to the invention.

The detectors 6 are connected with a computing unit 10 for evaluating the detected radiation spectra and intensities respectively via lines 9. The computing unit 10 is connected to other control devices and controllers via lines 11 for the purpose of transmitting the recorded data.

The detectors 6 comprise preferably a beam angle of approximately 90° as shown in the drawing, whereby the angle may be intentionally limited. Other beam angles and viewing angles respectively may be provided depending on type and shape of the room in which the processes take place. Larger beam angles, e.g. in the range exceeding 90°, are given preference in circular sections. Beam and viewing angles respectively for instance in ranges of ≦90° are useful in rectangular sections. Viewing angle resolutions may amount to angle minutes up to several degrees, even to 1°. The detectors are able to sense radiation from any radiation directions corresponding with the beam angle. A radiation incidenting along a radiation direction in a section 7 with one or several detecting zones 8 according to the invention is spectrally analyzed after detection in an optical facility by a spectrometer, e.g. by a grating or prism spectrometer, and imaged on a photon-sensitive detection matrix, e.g. a matrix array or a CCD chip, so that any spectra in section 7 with one or several detecting zone(s) 8 according to the invention are recorded.

The detection matrix comprises preferably a number of columns corresponding with the number of radiation directions, and a number of lines corresponding with the fineness of the spectral analysis. The structure of the detection matrix may also influence the spatial resolution of the detection.

With corresponding design of the detectors 6, especially of the optical device, the detecting zones 8 according to the invention may of course optionally be reduced in size and getting closer to individual points, thus improving the accuracy of the determination.

The detectors 6 determine essentially cumulative radiation intensities of wavelength ranges formed as band and band-free wavelength ranges, e.g. body and particle radiation respectively, and band radiation of radicals and molecules such as $C_2$, CH, CN, OH, NO, NH. A radiation spectrum continuously detected in such a way may comprise an ascending course towards larger wavelengths because of the superposition of both radiation types that are different from each other.

Signals corresponding with the detected radiation intensities are transmitted by the detectors 6 via lines 9 to the computing unit 10, whereby the signals take into account the radiation intensities cumulating in the conical sections 7 of the combustion chamber 2. The conical sections contain hereby one or several detecting zone(s) 8 according to the invention which comprise radicals with band radiation, and also substantially band-free body radiation emitted by dust and/or soot particles.

The integral radiation spectra of the sections 7 recorded in the computing unit 10 are tomographically evaluated, and temperature as well as concentration of radicals are determined in the detecting zones 8 according to the invention. The method of analyzing singular values is especially advantageous for the system of equations to be resolved to reconstruct local values.

One or several band-free wavelength ranges with associated local intensities are used according to the proportion pyrometry for the determination of local temperatures. Since this takes place for any radiation direction and any section 7 respectively, it corresponds with an n-dimensional ratio pyrometer.

In a first approach, the dust load influencing the intensity values is assumed to be homogeneously distributed in the combustion chamber 2 and a local intensity value is tomographically calculated for any detecting zone 8 according to the invention. The integration of the calculated intensity values serves then as correction allowance along a radiation direction. Provided that the dust load has been correctly estimated, the sum of tomographically reconstructed values corresponds with the particular value detected.

Then, local temperatures can be determined from the recorded local intensity values, eventually after repeated correction of the dust load, by formation of quotients. Hereby, it is considered to be as marginal condition that the temperature calculated from various formations of quotients for a location and a detecting zone 8 according to the invention must be identical within a certain deviation. If this is not the case, an iteration step with a correction of the dust load takes place.

For the determination of local concentrations of radicals, bands with associated intensity values of any radiation direction and any section 7 respectively, and the dust load known at this time is invoked, whereby high intensity values already point qualitatively to high concentrations of radicals. Local concentrations of radicals will then be determined tomographically.

A dust load known eventually from the temperature determination has the advantage that integral intensities along the radiation directions and in the sections 7 respectively can be easily corrected by absorption and/or extinction influences, whereafter radical concentrations are still to be determined tomographically. However, it is also possible to adopt assumptions and allowances respectively of the local dust load for temperature determination in order to determine the concentration, and to have both determination processes performed essentially in parallel.

A balancing step may be provided for checking the determined local values of temperature and radical concentrations, whereby local temperatures and band emission are checked for plausibility since a high temperature indicates a reaction zone and therefore a relatively high concentration of radicals. In furnaces for instance more CO tends to be present at low temperatures, and more $NO_x$ in reaction zones at high temperatures.

The method according to the invention permits to determine temperature and/or concentration conditions even on several levels of combustion chambers or reactors, thus enabling to determine other spatial non-inhomogeneities, and to obtain an even more comprehensive picture of processes and process conditions respectively. Therefore, other detectors for instance, eventually arranged in pairs, laterally and/or in parallel and/or in other disposition with respect to a first detector pair, may be provided.

Moreover, the determination and evaluation is not limited to the UV wavelength range, but is also possible in visible light up to infrared ranges.

The method according the invention is of great technical importance, e.g. for spectroscopic measurements in combustion chambers of coal-fired power plants, whereby radicals such as $C_2$, CH, CN and OH, which are of crucial importance in the kinetics of $NO_2$ formation, can be detected in spite of substantial parasitic influences originating from soot and dust radiation. The method permits in addition to record data and values respectively of multidimensional temperature and/or radical concentration fields which allow to intervene in processes at the primary side, so that for instance in furnaces substantial reductions of flue gas emission values of e.g. $NO_2$ and CO can be achieved. Furthermore, the contribution of for instance individual burners to the production of harmful substances, e.g. in a coal-fired plant comprising numerous burners, can be reconstructed, and radicals and molecules present in combustion chambers can be compared with estimates of reaction kinetics together with temperature distribution and flue gas analysis. The method provided permits also to analyze reactions in coal dust combustion participating in $NO_x$ formation and decomposition respectively, whereby for instance concentrations of the biatomic radicals OH, NH, CN, CH, which are of crucial importance, and of NO itself can be determined. In waste combustion for instance, dust concentrations correlating with concentrations of harmful substances, which substantially influence for instance the formation of 2,3,7,8 TCDD, can be determined in addition.

The detection of a reference radiation emitted from a reference radiator 12 radiating in a defined wavelength range is provided for temporary or permanent balancing and calibration respective of the detection and/or for improving the evaluation of the radiation spectrum. The wavelength range may therefore advantageous be outside of or also between the characteristic band radiation of radicals, which makes evaluation and identification easier.

However, the invention is not limited to the cited technical applications as already mentioned above.

We claim:

1. A method of determining characteristic features of a process that forms radicals within a process space comprising the steps of sensing with at least two spaced apart radiation detectors a radiation spectrum within the process space by detection of radiation intensity along various radiation directions; sensing the radiation spectrum along the various radiation directions in multiple zones within the process space, wherein said sensing the radiation spectrum comprises the steps of simultaneously detecting the radiation intensity of band radiation of multiple radicals within radical forming zones within the multiple zones along the various directions, and detecting the radiation intensity of body and particle radiation at band and band-free wavelength ranges within the multiple zones along the various radiation directions; integrating the radiation intensities within the multiple zones along the various radiation directions; and tomographically evaluating the radiation spectrum within crossing multiple zones to determine the characteristic features of the process.

2. A method according to claim 1 wherein the characteristic features of the process are temperature and concentration of radicals.

3. A method according to claim 1 including the step of limiting the radiation which enters the detectors.

4. A method according to claim 1 wherein each radiation detector has a beam angle of approximately 90°.

5. A method according to claim 1 including the step of detecting radiation from a reference radiator for calibration purposes.

6. A method according to claim 1 wherein the process space is within a combustion chamber or a reactor.

* * * * *